United States Patent [19]

Kane

[11] 4,252,128

[45] Feb. 24, 1981

[54] VISUAL PULSE INDICATOR

[76] Inventor: Donald D. Kane, 628 Live Oak Park Rd., Fallbrook, Calif. 92028

[21] Appl. No.: 70,161

[22] Filed: Aug. 27, 1979

[51] Int. Cl.³ .............................................. A61B 5/02
[52] U.S. Cl. .................................... 128/690; 40/21 C
[58] Field of Search ............................... 128/687–690, 128/678, 650; 73/748; 272/8 R, 8 D, 8 N; 40/21 C, 406, 407, 439, 477

[56] References Cited

U.S. PATENT DOCUMENTS

| 167,785 | 9/1875 | Pond | 128/689 |
|---|---|---|---|
| 1,782,328 | 11/1930 | Wearham | 40/406 X |
| 2,854,968 | 10/1958 | Wright | 128/690 |
| 3,090,377 | 5/1963 | Salisbury et al. | 73/748 X |
| 3,535,067 | 10/1970 | Lesher et al. | 128/690 X |
| 3,647,279 | 3/1972 | Sharpless | 272/8 D |
| 3,742,937 | 7/1973 | Manuel et al. | 128/690 |
| 3,898,781 | 8/1975 | Facchini | 272/8 D X |

FOREIGN PATENT DOCUMENTS 448325  1/1913  France .................................. 128/689

Primary Examiner—Lee S. Cohen
Attorney, Agent, or Firm—Arthur V. Doble

[57] ABSTRACT

A Visual Pulse Indicator, which may be placed directly over any area of the human body where an artery is near the surface of the skin, and includes the use of a transparent plate member, a flexible membrane and a fluid emulsion located between them. A peripheral member may also be located between the transparent member and the flexible membrane for further efficient containment of the fluid emulsion. The visual pulse indicator may be placed upon a person with the flexible membrane nearest the skin in the vicinity of any convenient pressure point such as that found in the wrist or the temple. The expansion of an artery, while absorbing a part of the pressure of the heart ventricles may be felt, and it is known as the pulse. This expansion produces movement of the artery, the skin, and even the flexible membrane of the Visual Pulse Indicator when in proper position. The pressure exerted through the flexible membrane against the transparent element produces a visual indication of the emulsion pattern change as it is disturbed in response to each beat, or arterial expansion.

7 Claims, 4 Drawing Figures

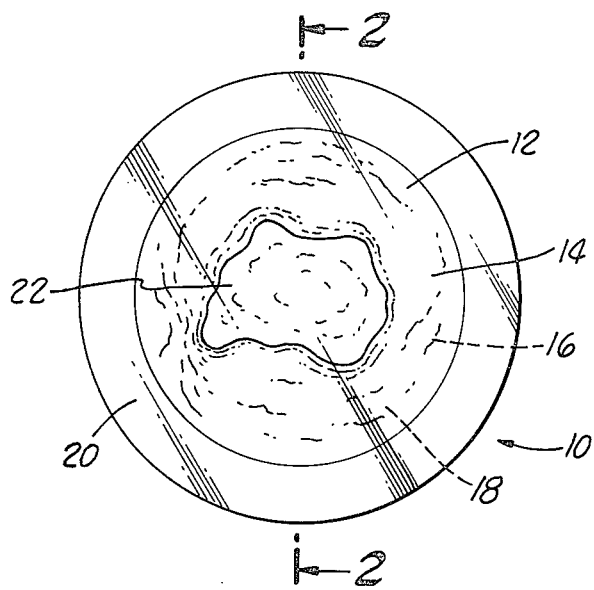
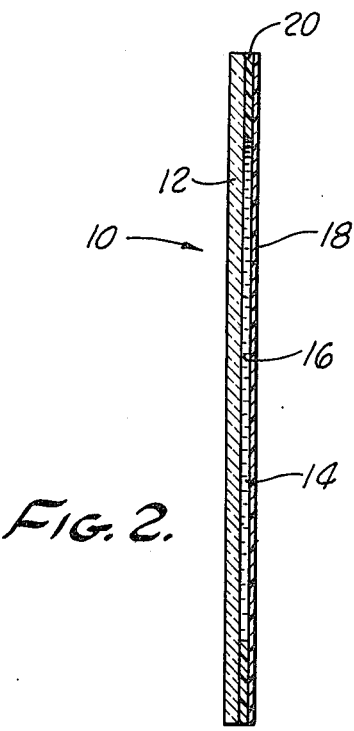
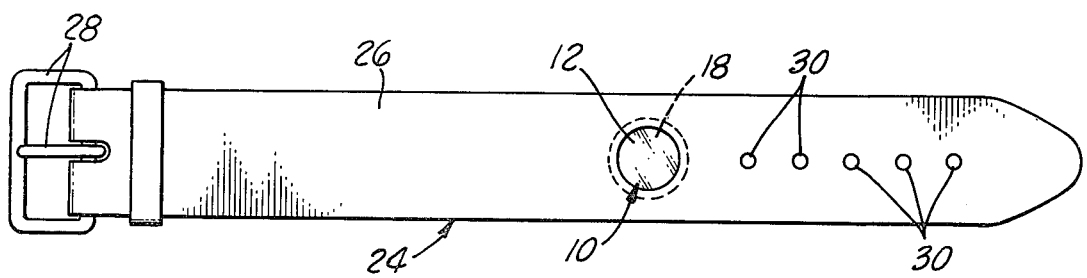
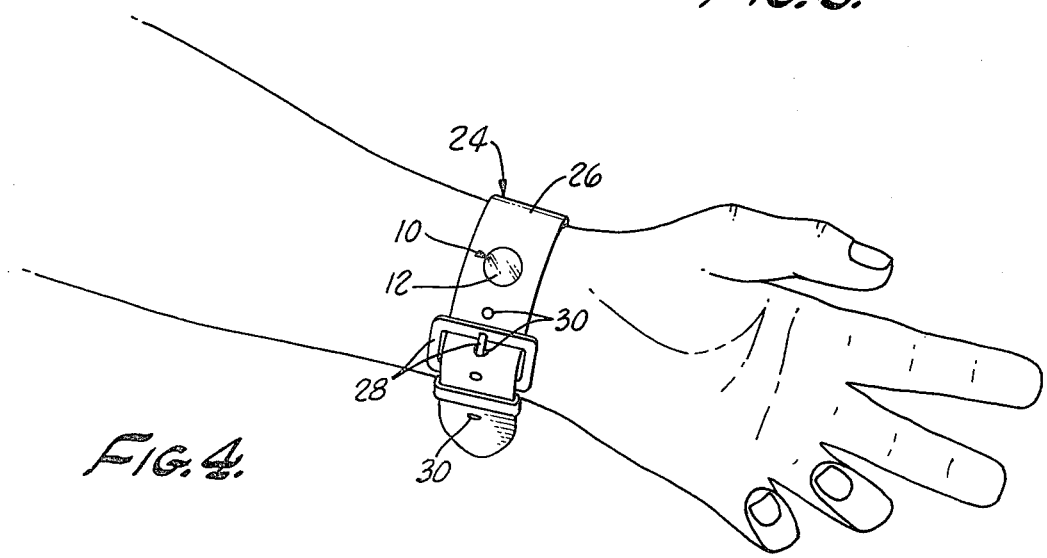

VISUAL PULSE INDICATOR

1. FIELD OF THE INVENTION

This invention generally relates to apparatus for the detection of blood circulation characteristics, and more particularly relates to an apparatus for providing a visual indication of heart-beat, or pulse.

2. PRIOR ART

A complete cycle of heart activity, or beat, consists of two phases; one of which is called the systole, and the other of which is known as the diastole. It is the first of these two phases, i.e. the systole, with which we are concerned. During the systole phase, the ventricles of the heart contract, thereby forcing blood into the arteries for the purpose of carrying blood awary from the heart to other parts of the body. Each contraction of the ventricles produce a surge of blood flowing through the arteries, and each such surge produces an expansion in the elastic arteries which absorb, in part, the pressure produced by said ventricle contraction.

The medical profession has ascertained that the rate of a person's heart-beat, or pulse, has great medical significance and that it is desirable to be able to detect the pulse easily and accurately. The pulse is felt quite readily at the wrist or the temple, and at any other part of the body which has the same rhythm as the heart beats. The usual method of feeling one's pulse at the wrist through the fingertips is a common practice which ordinarily produces good results. However, it is not a flawless system because the strength of the pulse of each person varies within limits and is sometimes difficult to detect for a number of biological reasons.

Accordingly, scientists have developed various types of pulse detection devices for use by the medical profession. The known prior art activity has been directed primarily to "pressure-sensing" devices. Included among these devices are the inventions disclosed in the following United States Patents, having numbers:

A close examination of each of the above patents reveals that they disclose pressure-sensing devices or related systems, which are generally adapted for wearing on the wrist, but none of the known prior art relates to a direct visual indication of pulse.

Each of the above-patented devices are moderately complicated inventions which utilize a multiplicity of parts and components, and which can only be manufactured at considerable expense. The administration of their use must also be done with great care in order to obtain meaningful results.

SUMMARY OF THE INVENTION

Applicant herein has conceived of a new visual pulse indicator which may be placed directly over any pressure point of the human body. The visual pulse indicator produces an accentuation of the motion of the artery and skin at the pressure point area caused by each beat.

This new and useful invention is an article of manufacture and includes the use of a transparent plate member, a thin flexible membrane and a fluid emulsion sealed in the pocket formed therebetween. Use may be made of a thin peripheral member between the transparent member and the flexible membrane for impoved containment of the fluid emulsion.

As this visual pulse indicator is placed over a common pressure point such as the wrist or the temple, with the flexible membrane next to the skin, the expansion of the artery produces motion of the skin and the adjoining tissues and causes a visual enhancement of said motion in the form of pattern or color changes in the emulsion, which may be viewed through the transparent plate member, as it is disturbed in response to each beat, or arterial expansion.

This visual pulse indicator may be applied to a pressure point in any of several convenient ways, among which are included: the placement and holding of the pulse indicator directly on a pressure point by manual means, i.e. the use of hand-pressue; the attachment over the skin at the pressure point by means of adhesive tape or its equivalent; the placement of the visual pulse indicator in an ordinary wrist-strap of the type used for watches whereby the visual pulse indicator is positioned over the wrist pressure-point and conveniently held in place by the strap; or by any other convenient means.

The present invention shows several features of novelty over the known prior art, including the capability for providing a non-invasive visual pulse indication without the use of complex, expensive pressure-sensing systems with remote readout apparatus or electronic signal processors or converters.

It is therefore an object of this invention to provide a visual pulse indicating device for placement over a pressure point on a human body for a direction visual indication of pulse or heart beat.

It is another object of this invention to provide a visual pulse-indicating device which is simply manufactured using a transparent plate member, a flexible membrane, and a small quantity of fluid emulsion or oil located therebetween.

It is another object of this invention to provide a visual pulse-indicating device which may be manufactured using a transparent plate member, a flexible membrane, an emulsion or oil located therebetween, and a peripheral member located between the transparent plate and the flexible membrane for further and efficient containment of the emulsion or oil.

It is another object of the present invention to provide a visual pulse-indicating device which is easy to wear by any person, and for convenient and rapid use by any layman or medical person.

It is another object of this invention to provide a visual pulse-indicating device which is lightweight, durable, rugged, reliable and very inexpensive to manufacture.

It is another object of this invention to provide a visual pulse-indicating device which is set into a wrist-strap and adapted to be easily worn by a person whose pulse is to be visually indicated.

For a better understanding of this present invention, together with other and further objects thereof, reference is made to the following description taken in connection with the accompanying drawings in which the preferred embodiments of this invention are illustrated, the scope of the invention being pointed out and contained in the appended claims.

BRIEF DESCRIPTION OF THE DRAWINGS

FIG. 1 is a front view of one embodiment of the invention showing a disturbed fluid emulsion pattern under the surface of a transparent plate member.

FIG. 2 is a cross-sectional view taken along the line 2—2 of FIG. 1 during an undisturbed time.

FIG. 3 is a perspective view of a small-sized version of the device shown in FIG. 1 having been imbedded in a wrist-strap.

FIG. 4 is a perspective view of the embodiment shown in FIG. 3 being worn on a person's wrist for a pulse indication.

DESCRIPTION OF THE PREFERRED EMBODIMENTS

In FIG. 1 at 10 these is shown a preferred embodiment of this visual pulse indicator. A transparent plate member 12 faces the viewer of this figure and extends across the entire front surface of pulse indicator 10. A fluid emulsion 14 is located in a pocket 16 beneath the surface of transparent plate member 12 and is contained in pocket 16 by the use of a flexible membrane 18 which may be made out of any convenient, oil-resistant, tough, durable, flexible material such as high-strength plastics, vinyls or rubber compounds. The fluid emulsion 14 may be of any convenient substance which, when encapsulated, produces a visible pattern change or spectral dispersion when disturbed by an external force. Flexible membrane 18 is permanently joined or cemented, at its edges, to the outer edges of member 12 or optional peripheral member 20. Member 20 is attached to member 12 and may be of any convenient shape and is useful in the manufacturing of the pulse indicator 10 by forming with member 12 a very shallow pocket 16 for containment of the fluid emulsion 14. The flexible membrane 18 is generally made opaque for best results to aid in the observation of the random patterns created by the fluid emulsion 14 as seen through the transparent member 12.

Whenever a force is applied to the outside surface of the flexible membrane 18, a disturbance is created within the pocket 16 and an observer can readily see changes in the patterns appearing below the face of transparent member 12 each time that a force is applied at or removed from the flexible membrane 18. The number of changes in the patterns correspond to the pulse, or heart beat rate.

In FIG. 2 there is shown a cross-sectional view of the visual pulse indicator taken along the line 2'2 of FIG. 1. Transparent plate member 12 is shown at the left and flexible membrane 18 is shown at the right. Pocket 16 is here defined by member 12 and the inner edges of peripheral membrane 20. The use of this peripheral member is optional. The emulsion 14 is located in pocket 16 and flexible membrane 18 caps the pocket 16 for encapsulation of the fluid emulsion 14 therein.

In FIG. 3 there is shown at 24 one preferred embodiment of this invention. This wrist-strap-assembly 24 embodiment of the invention includes a simple wrist-strap 26 with its typical fastening means 28 and corresponding holes 30 for cooperative use with fastening means 28. It further includes, as its primary purpose the embedding of a visual pulse indicator 10 of the type shown in its enlarged view in FIG. 1 with flexible membrane 18 being exposed at the lower surface of strap 26. FIG. 4 demonstrates that this assembly 24 is constructed in such a way and is intended to be worn in a manner whereby flexible membrane 18 may be placed next to a person's skin in the wrist area directly over an artery to respond to the pulse as described hereinabove.

It is to be understood that while the detailed drawings and specific examples given herein describe preferred embodiments of the invention, they are for purposes of illustration only, and that the invention is not limited to the precise details and conditions disclosed and that various changes may be made therein, without departing from the spirit of the invention which is defined by the following claims.

What is claimed is:

1. A visual pulse indicator which may be placed over any of several common arterial pressure points on a person's body for converting the motion of an expanding and contracting artery beneath the skin into easy-to-see patterns changing in response to the pulse, said visual pulse indicator comprising:
    (a) a transparent plate member through which said patterns may be observed;
    (b) a flexible membrane joined at its outer areas to the outer areas of said transparent plate member defining a closed pocket between said flexible membrane and said plate member, the flexible membrane adapted to be placed next to the person's skin and moved in response to the motion of the adjacent skin and underlying artery;
    (c) a fluid emulsion located in said closed pocket between the flexible membrane and said plate member for providing patterns visible through the transparent plate member, the patterns being changeable in response to movement of the flexible membrane caused by the pulse; and
    (d) a wrist-strap in which the plate member, the flexible membrane and the fluid emulsion are positioned to facilitate wearing of the pulse indicator on the wrist with said flexible membrane being placed next to the person's skin and underlying artery.

2. A visual pulse indicator which may be placed over any of several common arterial pressure points on a person's body for converting the motion of an expanding and contracting artery beneath the skin into easy-to-see patterns changing in response to the pulse, said visual pulse indicator comprising:
    (a) a transparent plate member through which said patterns may be observed;
    (b) a peripheral member joined with the transparent plate member at the outer area of said plate member defining a pocket capable of containing a liquid;
    (c) a flexible membrane joined at its outer areas with the peripheral member, defining a closure to said pocket formed by said transparent plate member and said peripheral member;
    (d) a fluid emulsion located in said pocket between the flexible membrane, the peripheral member and the transparent plate member for providing patterns visible through the transparent plate member, the patterns being changeable in response to movement of the flexible membrane caused by the pulse; and
    (e) a wrist-strap in which the plate member, the peripheral member, the flexible membrane and the fluid emulsion are positioned to facilitate wearing of the pulse indicator on the wrist with said flexible membrane being placed next to the person's skin and underlying artery.

3. The visual pulse indicator of claim 2, above, wherein the flexible membrane is opaque to accentuate the visible patterns which change in response to movement of said flexible membrane.

4. The visual pulse indicator of claim 2, above, wherein the transparent plate member is circular in shape.

5. The visual pulse indicator of claim 2, above, wherein said peripheral member is circular in shape.

6. The visual pulse indicator of claim 2, above, wherein the fluid emulsion causes spectral dispersion visible through said transparent plate member when disturbed by movement of said flexible membrane as it is disturbed by the pulse.

7. A visual pulse indicator which may be placed over any of several common arterial pressure points on a person's body for converting the motion of an expanding and contracting artery beneath the skin in easy-to-see patterns changing in response to the pulse, said visual indicator comprising:
(a) a transparent plate member through which said patterns may be observed;
(b) a peripheral member joined with the transparent plate member at the outer area of said plate member defining a shallow pocket capable of containing a fluid emulsion;
(c) a flexible membrane joined at its outer areas with the peripheral member defining a closure to the pocket formed by said transparent plate member and said peripheral member, the flexible membrane being opaque to accentuate patterns visible through said plate member;
(d) a fluid emulsion located in said shallow pocket between the flexible membrane, the peripheral member and the transparent plate member for providing patterns which are visible through the plate member and which are changeable in response to movement of the flexible membrane; and
(e) a wrist-strap in which the plate member, the peripheral member, the flexible membrane and the fluid emulsion are positioned to facilitate wearing of the pulse indicator on the wrist with said flexible membrane being placed next to the person's skin and underlying artery.

* * * * *